US011925466B2

(12) United States Patent
Vitale et al.

(10) Patent No.: US 11,925,466 B2
(45) Date of Patent: Mar. 12, 2024

(54) IMPLANTABLE DEVICES USING 2D METAL CARBIDES AND NITRIDES (MXENES)

(71) Applicants: THE TRUSTEES OF THE UNIVERSITY OF PENNSYLVANIA, Philadelphia, PA (US); Drexel University, Philadelphia, PA (US)

(72) Inventors: Flavia Vitale, Wilmington, DE (US); Brian Litt, Bala Cynwyd, PA (US); Nicolette Driscoll, Philadelphia, PA (US); Yury Gogotsi, Ivyland, PA (US); Babak Anasori, Fisher, IN (US); Kathleen Maleski, Mount Airy, MD (US)

(73) Assignees: The Trustees of the University of Pennsylvania, Philadelphia, PA (US); Drexel University, Philadelphia, PA (US)

( * ) Notice: Subject to any disclaimer, the term of this patent is extended or adjusted under 35 U.S.C. 154(b) by 791 days.

(21) Appl. No.: 16/646,662

(22) PCT Filed: Sep. 14, 2018

(86) PCT No.: PCT/US2018/051084
§ 371 (c)(1),
(2) Date: Mar. 12, 2020

(87) PCT Pub. No.: WO2019/055784
PCT Pub. Date: Mar. 21, 2019

(65) Prior Publication Data
US 2020/0405165 A1    Dec. 31, 2020

Related U.S. Application Data
(60) Provisional application No. 62/559,315, filed on Sep. 15, 2017.

(51) Int. Cl.
*A61N 1/05* (2006.01)
*A61B 5/24* (2021.01)
(Continued)

(52) U.S. Cl.
CPC ............... *A61B 5/283* (2021.01); *A61B 5/24* (2021.01); *A61B 5/296* (2021.01); *A61N 1/05* (2013.01)

(58) Field of Classification Search
CPC ........... A61B 5/283; A61B 5/24; A61B 5/296; A61N 1/05; A61N 1/08; A61N 1/36125;
(Continued)

(56) References Cited

U.S. PATENT DOCUMENTS

2005/0111165 A1 *  5/2005  Merker ................... H01G 9/10
                                                          361/525
2010/0161019 A1 *  6/2010  Clark ....................... A61B 5/24
                                                          607/116
(Continued)

FOREIGN PATENT DOCUMENTS

JP      2017-076739 A    4/2017
JP      6185638 B1       8/2017
(Continued)

OTHER PUBLICATIONS

Xu, Bingzhe, et al. "Ultrathin MXene-Micropattern-Based Field-Effect Transistor for Probing Neural Activity." Advanced Materials (Weinheim), vol. 28, No. 17, 2016, pp. 3333-3339, https://doi.org/10.1002/adma.201504657. (Year: 2016).*
(Continued)

*Primary Examiner* — Carl H Layno
*Assistant Examiner* — Anh-Khoa N Dinh
(74) *Attorney, Agent, or Firm* — BakerHostetler

(57)    ABSTRACT

An electrode, the electrode including an exposed contact surface, the exposed surface comprising a contact material,
(Continued)

the contact material comprising a MXene. A device, the device including a plurality of electrodes, each of the plurality of electrodes comprising an exposed contact surface, the exposed surface comprising a contact material, the contact material comprising a MXene. A method, the method including delivering electrical stimulation to a subject with an electrode that comprises an exposed contact surface, the exposed contact surface comprising a contact material that includes a MXene.

20 Claims, 24 Drawing Sheets

(51) Int. Cl.
    *A61B 5/283*     (2021.01)
    *A61B 5/296*     (2021.01)

(58) Field of Classification Search
    CPC ....... A61N 1/0529; A61L 27/30; A61L 27/40; H05K 1/092; H05K 2201/0245; H05K 2201/0323; H05K 2203/0285; H05K 2203/095; H05K 2203/1366; H05K 3/125; H05K 3/1291; H05K 3/146; C09D 11/033; C09D 11/037; C09D 11/52
    See application file for complete search history.

(56) References Cited

U.S. PATENT DOCUMENTS

| | | |
|---|---|---|
| 2012/0029585 A1 | 2/2012 | Pickett |
| 2014/0162130 A1* | 6/2014 | Barsoum ............... C01B 32/914 429/231.8 |
| 2016/0007874 A1 | 1/2016 | Ma et al. |

FOREIGN PATENT DOCUMENTS

| | | |
|---|---|---|
| WO | 2012/177712 A1 | 12/2012 |
| WO | 2014/088995 A1 | 6/2014 |
| WO | 2016/049109 A2 | 3/2016 |
| WO | 2016/140948 A1 | 9/2016 |
| WO | 2017/011044 A2 | 1/2017 |

OTHER PUBLICATIONS

Liu, Hui, et al. "A Novel Nitrite Biosensor Based on the Direct Electrochemistry of Hemoglobin Immobilized on MXene-Ti3C2." Sensors and Actuators. B, Chemical, vol. 218, 2015, pp. 60-66, https://doi.org/10.1016/j.snb.2015.04.090. (Year: 2015).*

Liu et al., "A Novel nitrite biosensor based on the direct electrochemistry of hemoglobin immobilized on MXene-Ti3C2", Sensors and Actuators B 218 (2015) 60-66 (2015), p. 61, online https://www.sciencedirect.com/science/article/pii/S0925400515005420.

Lukatskaya, et al., Ultra-high-rate pseudocapacitive energy storage in two-dimensional transition metal carbides, Nature Energy, 2017, 6, 17105.

Xu et al., "Ultrathin MXene-Micropattern-Based Field-Effect Transistor for Probing Neural Acivity", Adv. Mater. 2016, 28, 3333-3339 (2016), p. 3333, online https://onlinelibrary.wiley.com/doi/abs/10.1002/adma.201504657.

Vitale eta l., "Neural Stimulation and Recording with Bidirectional, Soft Carbon Nanotube Fiber Microelectronics", ACS Nano, 2015, vol. 9, No. 4, 4465-4474.

* cited by examiner

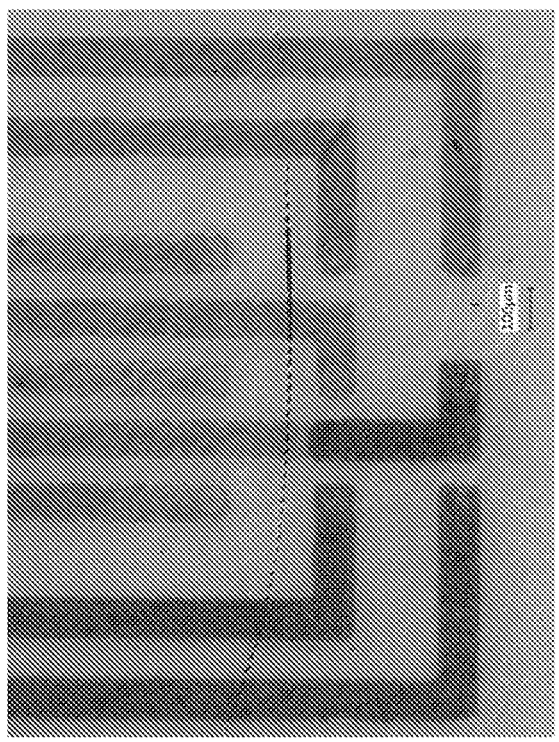
Fig. 5B MXene/PEDOT
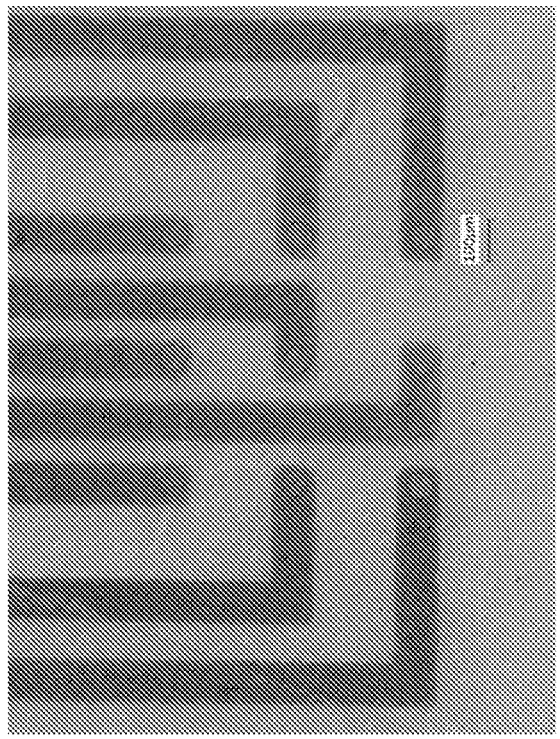
Fig. 5A MXene

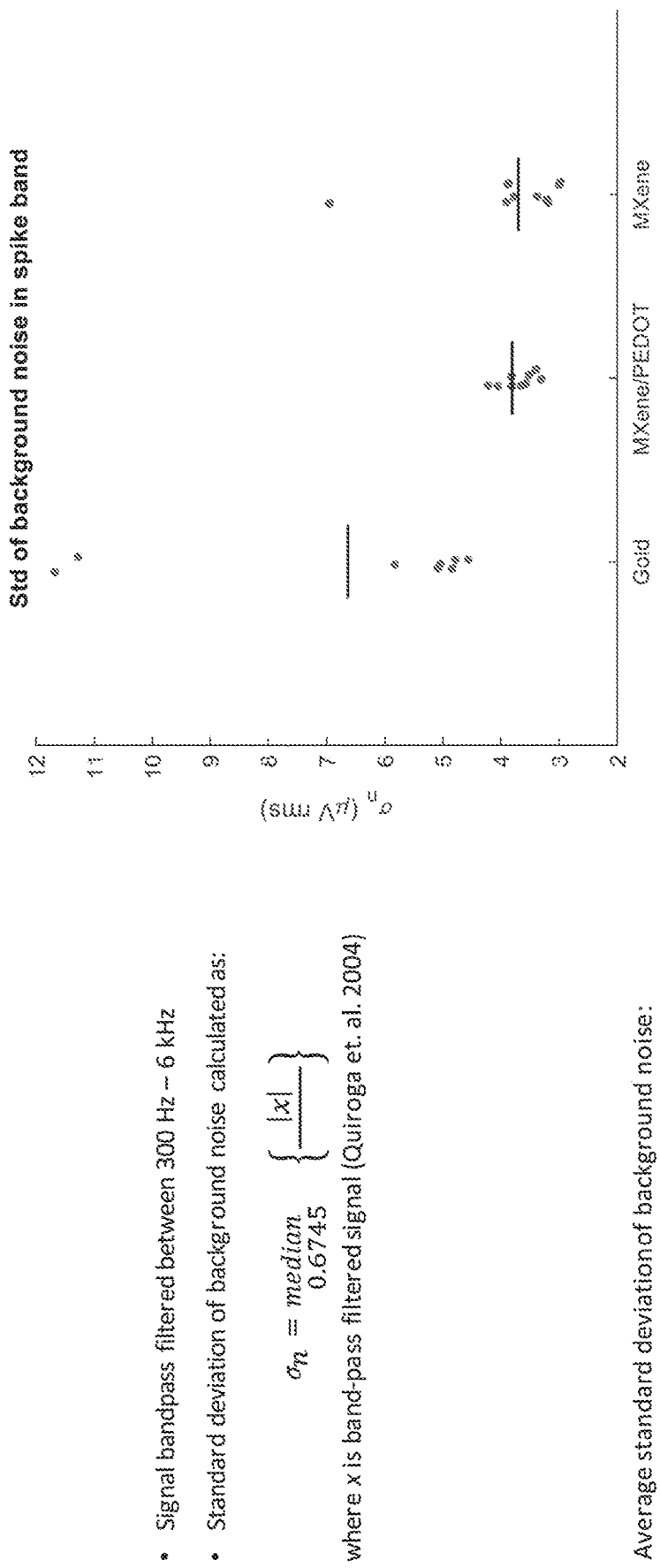

Fig. 9

Spike band noise comparison

Spikeband — the frequency range where we would expect to see individual neuron spiking activity (units)

Comparison of noise level in the spike band between the different devices:

- Signal bandpass filtered between 300 Hz – 6 kHz
- Standard deviation of background noise calculated as:

$$\sigma_n = median\left\{\frac{|x|}{0.6745}\right\} \text{(Quiroga et. al. 2004)}$$

where x is band-pass filtered signal (Quiroga et. al. 2004)

Average standard deviation of background noise:

Gold    6.6 µV rms
MXene/PEDOT   3.8 µV rms
MXene   3.7 µV rms

Transparent Mxene neural sensors

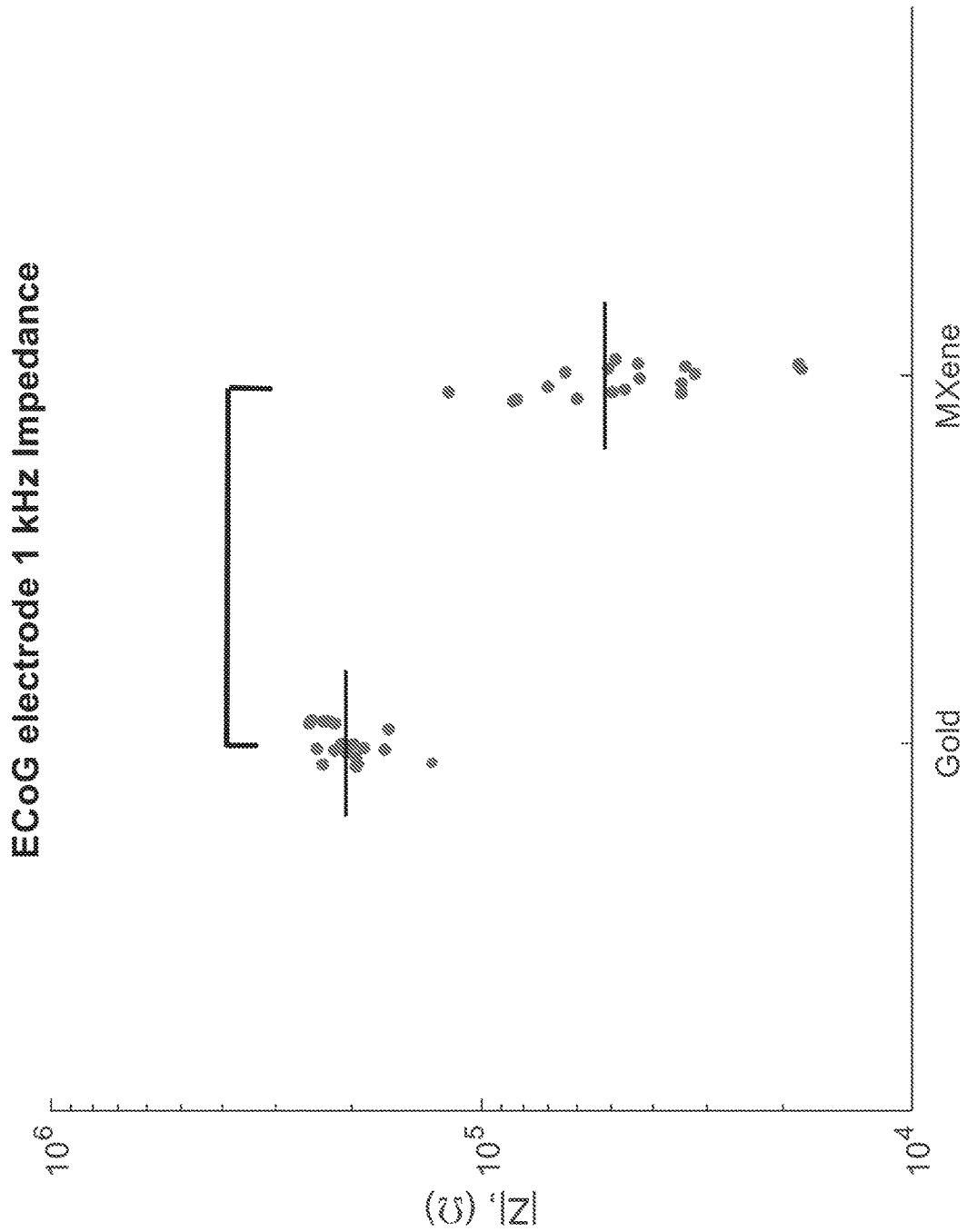

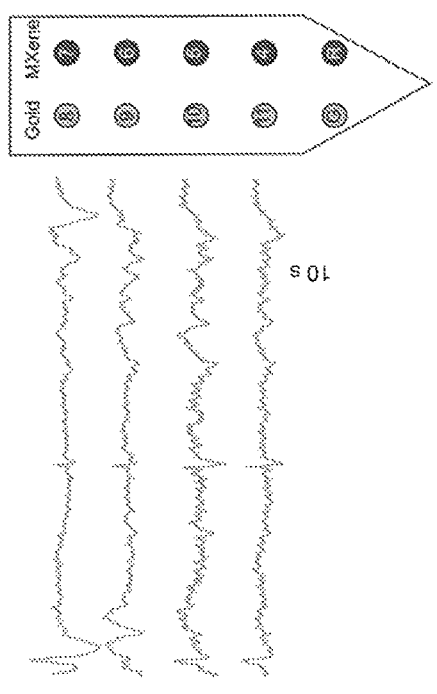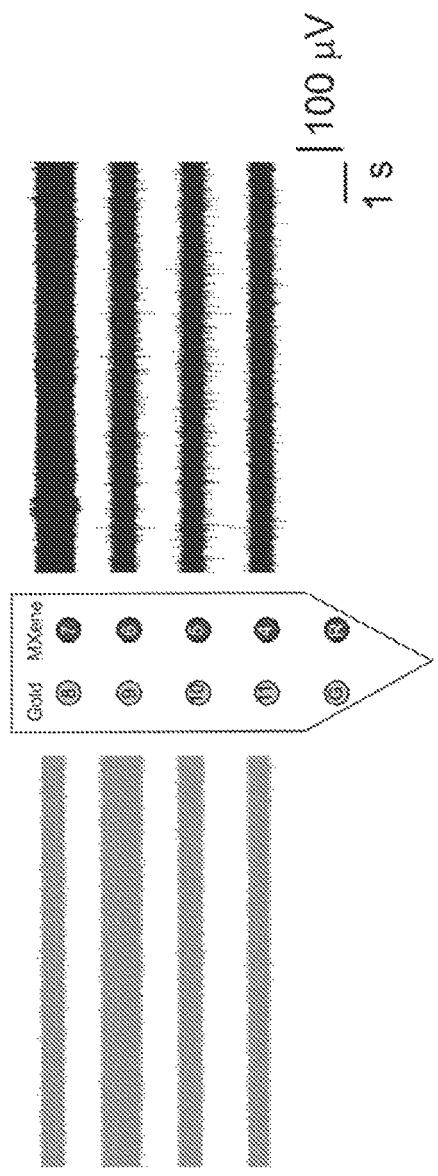
Fig. 15A-1
Fig. 15A-2

IMPLANTABLE DEVICES USING 2D METAL CARBIDES AND NITRIDES (MXENES)

CROSS-REFERENCE TO RELATED APPLICATIONS

This application is the National Stage Application of International Patent Application No. PCT/US2018/051084, filed Sep. 14, 2018, which application claims the benefit of U.S. Provisional Application Ser. No. 62/559,315, filed Sep. 15, 2017, entitled "Implantable Devices Using 2D Metal Carbides and Nitrides (MXenes)", the entireties of which applications are hereby incorporated herein by reference for any and all purposes.

TECHNICAL FIELD

This disclosure pertains to electrodes for electrical sensing and stimulation of biological tissue.

BACKGROUND

Traditional implantable devices for recording and stimulating body electrical activity are fabricated with metal-based components using materials such as platinum, iridium, stainless steel, and the like. However, such metals can be poorly matched to the electrical, mechanical and chemical properties of biological tissues and pose several issues for long-term implantation and functionality of these devices, including scarring, inflammation, degradation, and fatigue.

Furthermore, the electrochemical impedances and charge storage capacities of metals is typically inadequate to achieve good quality recording and stimulation performance. Most conductive materials currently used for neural interfaces, for example, result in microscale electrodes with impedances that are considerably higher than what may be desired or acceptable range for certain purposes. The high impedance results in significant noise interference and inadequate signal-to-noise (SNR) to resolve which signal comes from which from individual neurons.

Improving electrochemical properties of metal-based electrodes typically requires either increasing the electrode size and invasiveness or adding metal or electroactive polymer coatings to achieve adequate electrochemical properties. This additional coating layer poses safety issues, such as increasing the risk of harmful toxic effects caused by electrode degradation in the tissue. Further, metals are optically opaque and interfere with optical stimulation modalities, which is a major roadblock for the development of multimodal optoelectronic devices. Accordingly, there is a long-felt need in the art for improved electrode devices, in particular for such devices configured for monitoring neural activity.

SUMMARY

In meeting the above-described needs, the present disclosure provides electrodes, comprising an exposed contact surface, the exposed surface comprising a contact material, the contact material comprising an MXene.

The present disclosure also provides methods, comprising using an electrode according to the present disclosure in connection with monitoring one or more signals related to neural activity, muscular activity, cardiac activity, or combinations thereof Additionally provided are methods, the methods comprising incorporating an electrode according to the present disclosure into a device that is configured to perform monitoring and stimulating one or more signals related to neural activity, muscular activity, cardiac activity, or combinations thereof.

BRIEF DESCRIPTION OF THE FIGURES

FIGS. 5A and 5B are photographs of example prototype devices.

FIGS. 6A and 6B show potentiostatic EIS in phosphate buffered saline (PBS), which is similar in ionic concentration and conductivity to cerebrospinal fluid (CSF). Measurements were taken with a three electrode configuration with Ag/AgCl reference electrode, graphite rod counter electrode and a 20 mVrms excitation.

FIGS. 8A, 8B, and 8C show LFPs recorded in vivo in an anesthetized rat. Power spectral density shows clear slow (~1-2 Hz) and gamma (~40-70 Hz) oscillation power, which is expected for a rat under ketamine-dexmetomidine anesthesia.

FIG. 9 shows a spike band noise comparison of illustrative devices.

FIGS. 13A and 13B are graphs of impedance characterizations for example depth electrodes.

FIGS. 15A and 15B illustrate recordings in spike bands made with example electrodes.

DETAILED DESCRIPTION

Figure 1A:
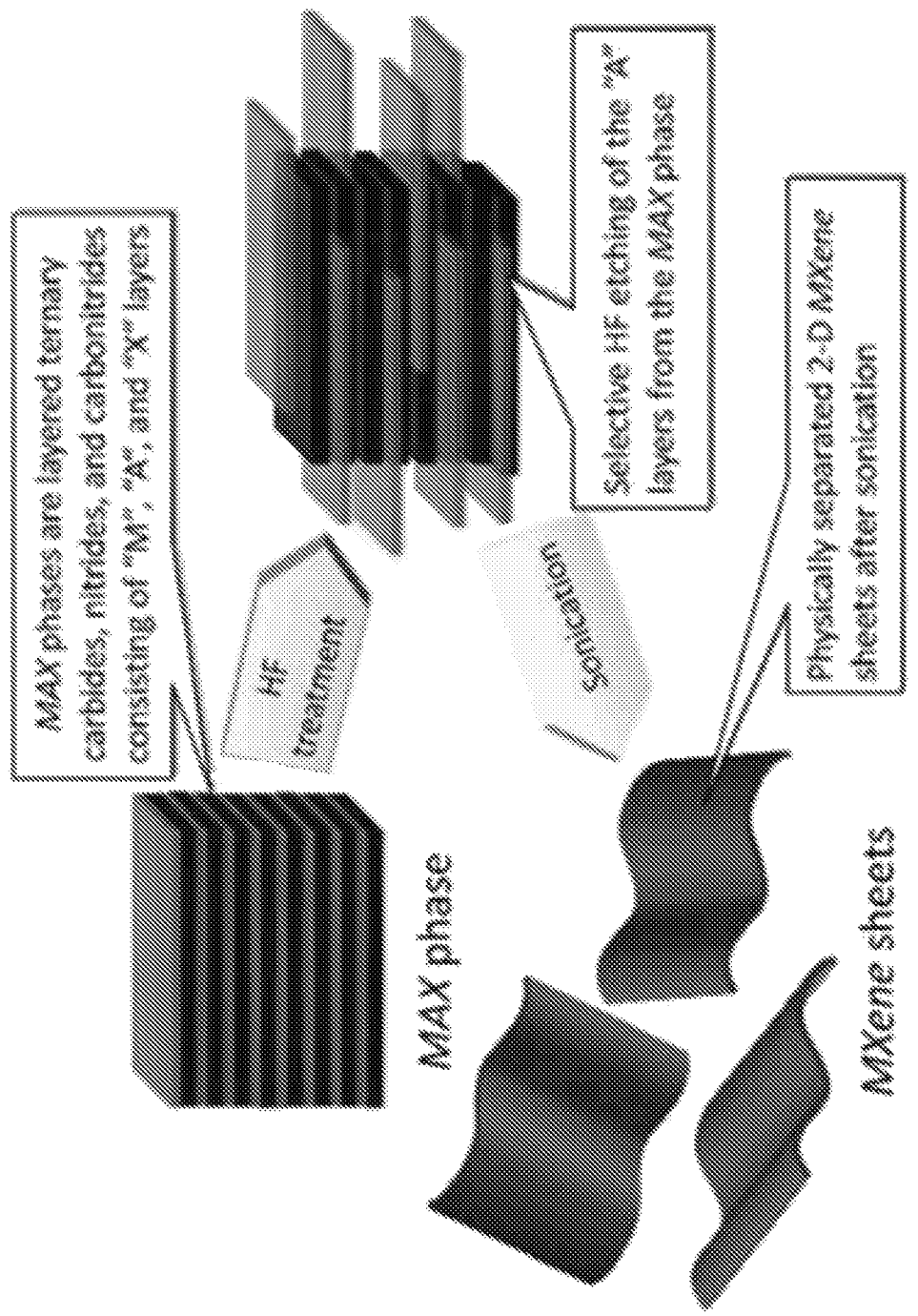
FIG. 1A describes MXene materials.
Figure 1B:
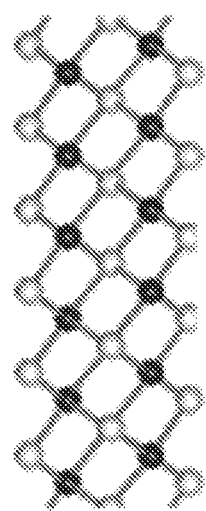
FIG. 1B illustrates a two-dimensional (2D) MXene lattice.
Figure 2:
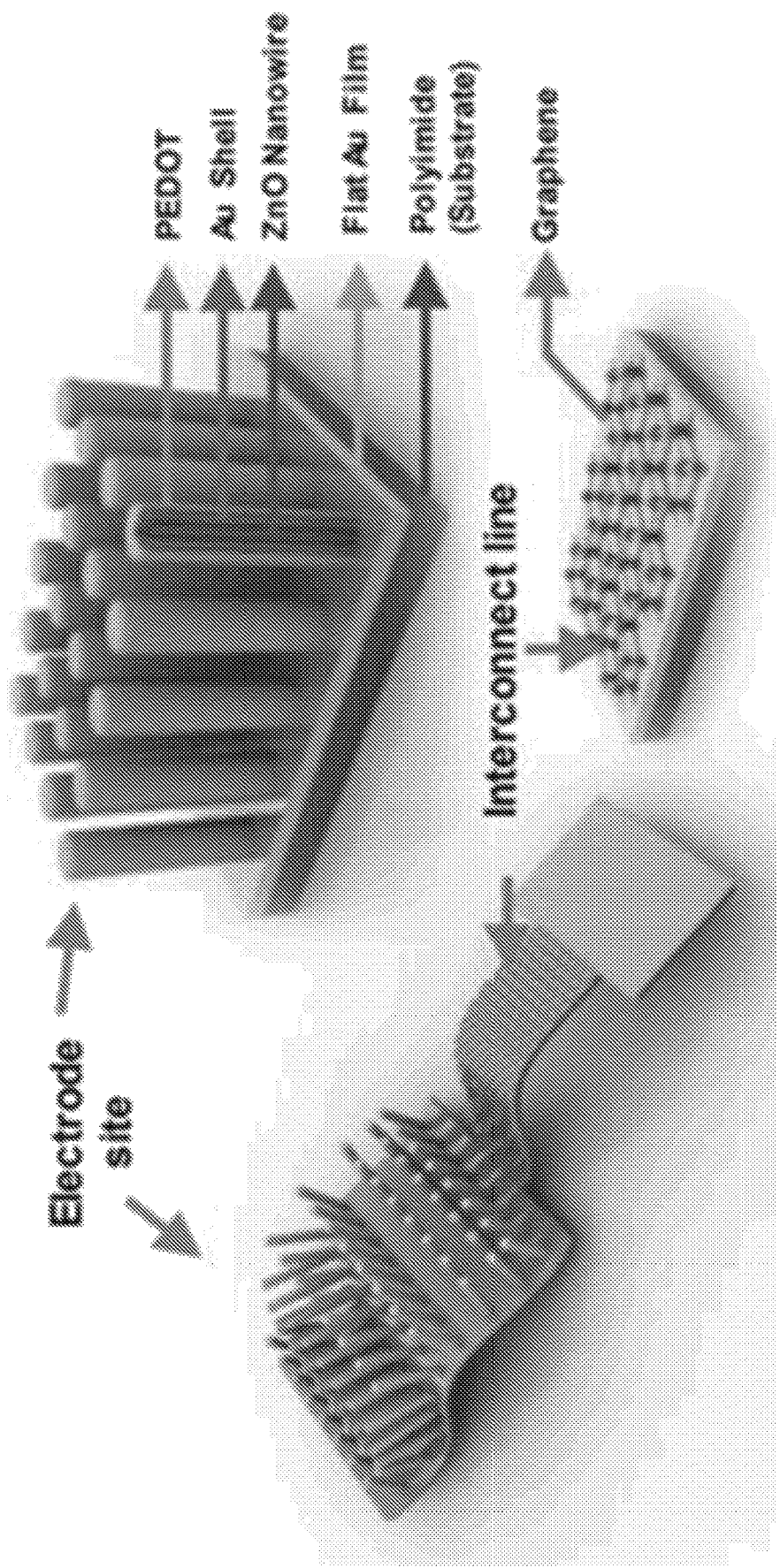
FIG. 2 describes metallic electrodes.
Figure 3:
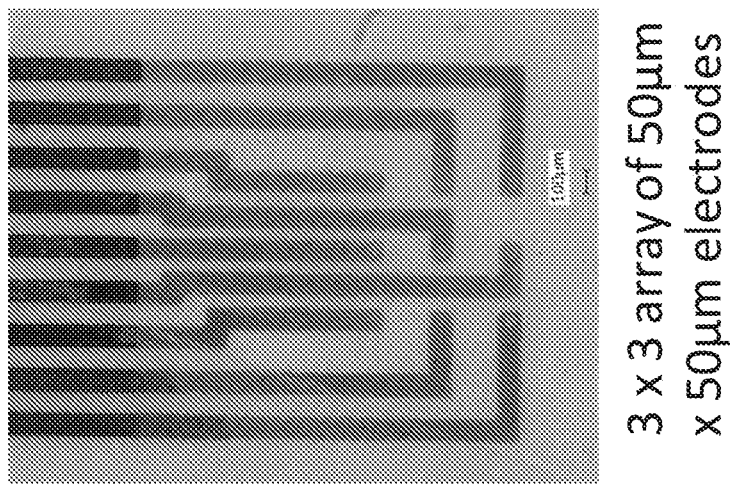
FIG. 3 describes testing of MXene electrodes.
Figure 4:
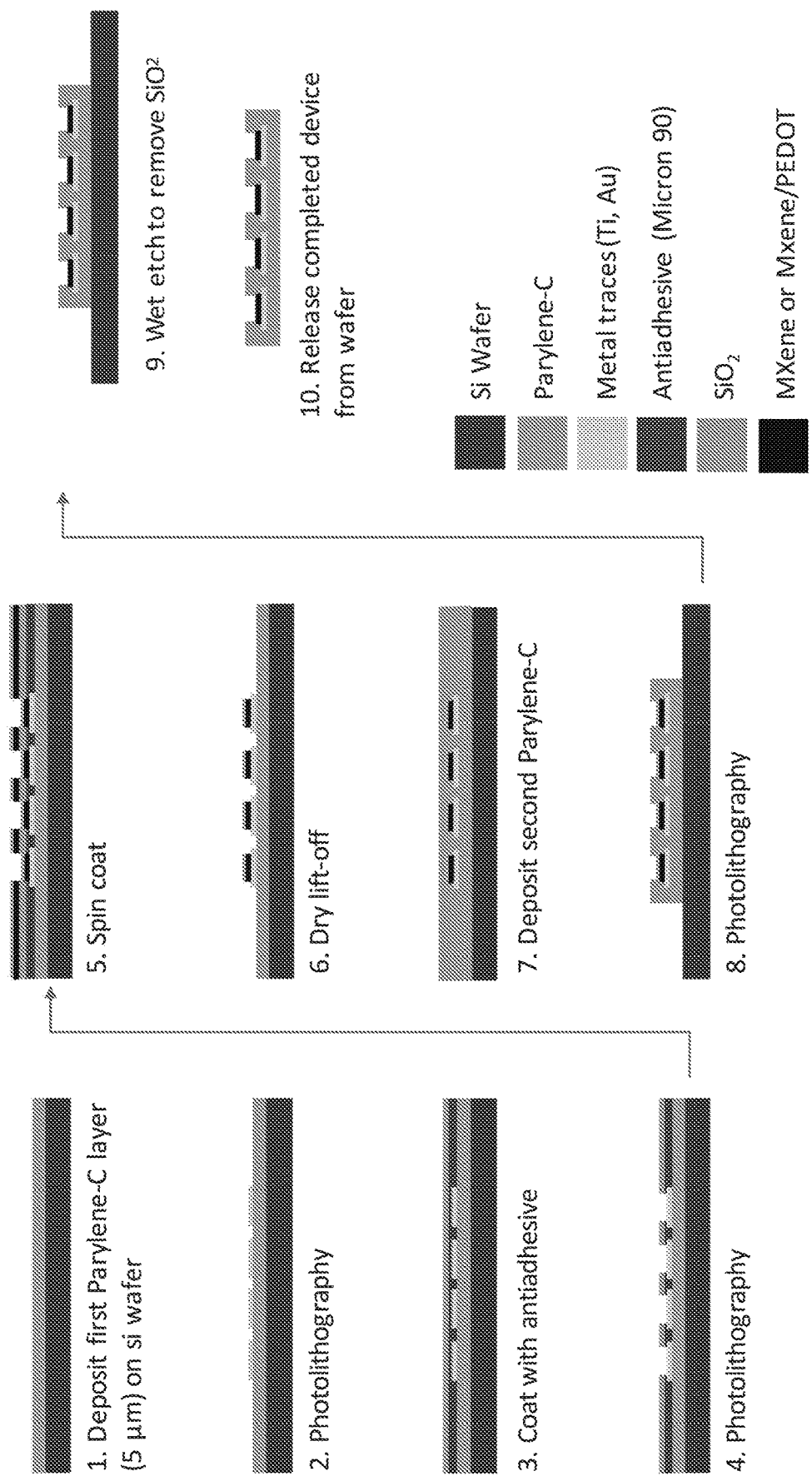
FIG. 4 illustrates an exemplary process for creating MXene electrodes.
Figure 6A:
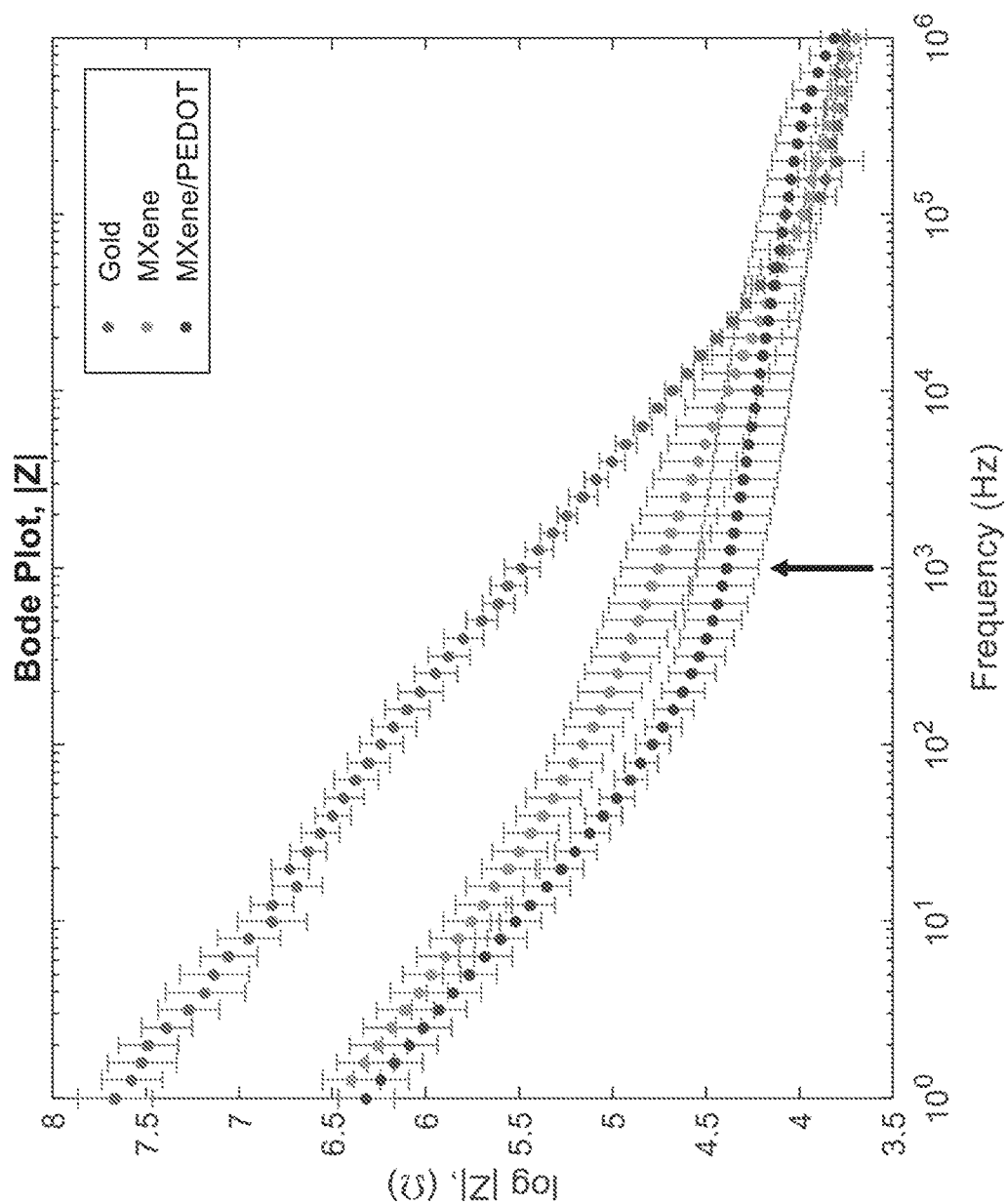
FIGS. 6A and 6B shows example results of electrochemical characterization of example prototype devices.
Figure 6B:
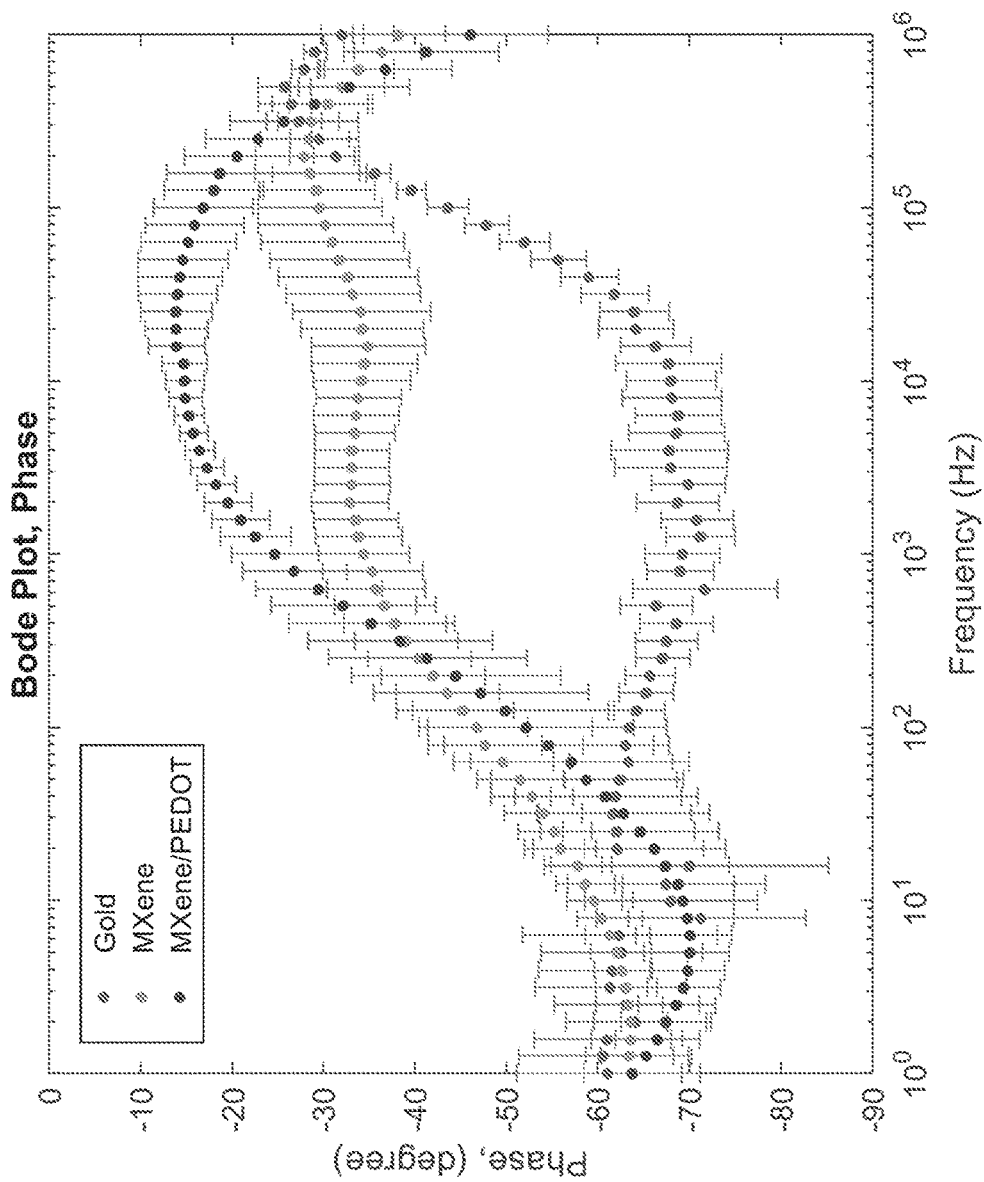
Figure 7:
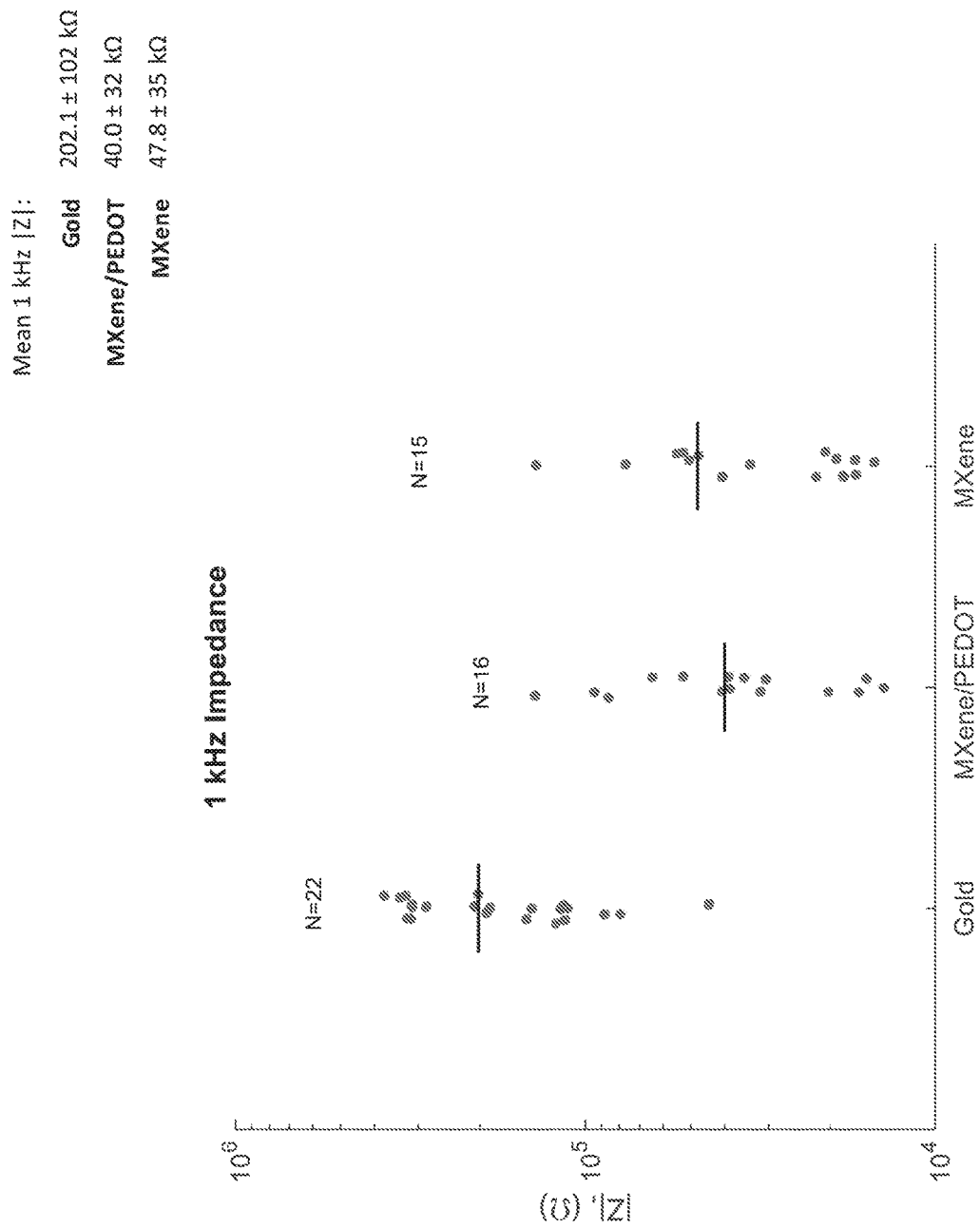
FIG. 7 illustrates impedance testing results of illustrative devices.
Figure 8A:
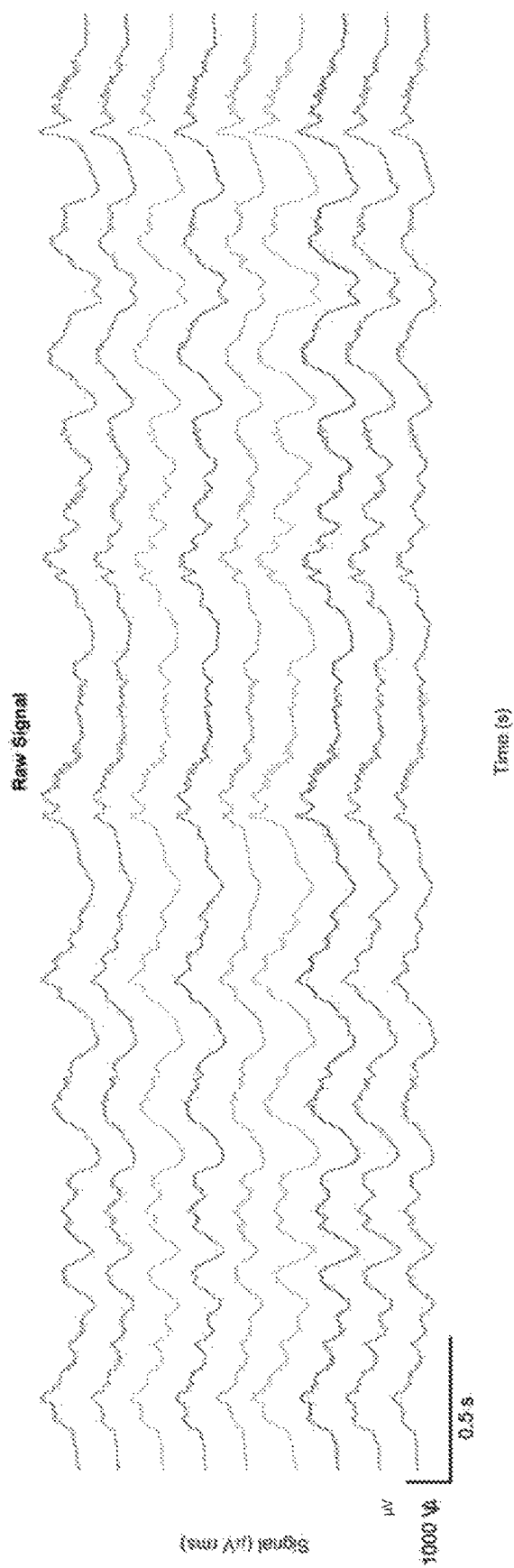
FIGS. 8A, 8B, and 8C shows time and frequency charts of data obtained with example prototype devices.
Figure 8B:
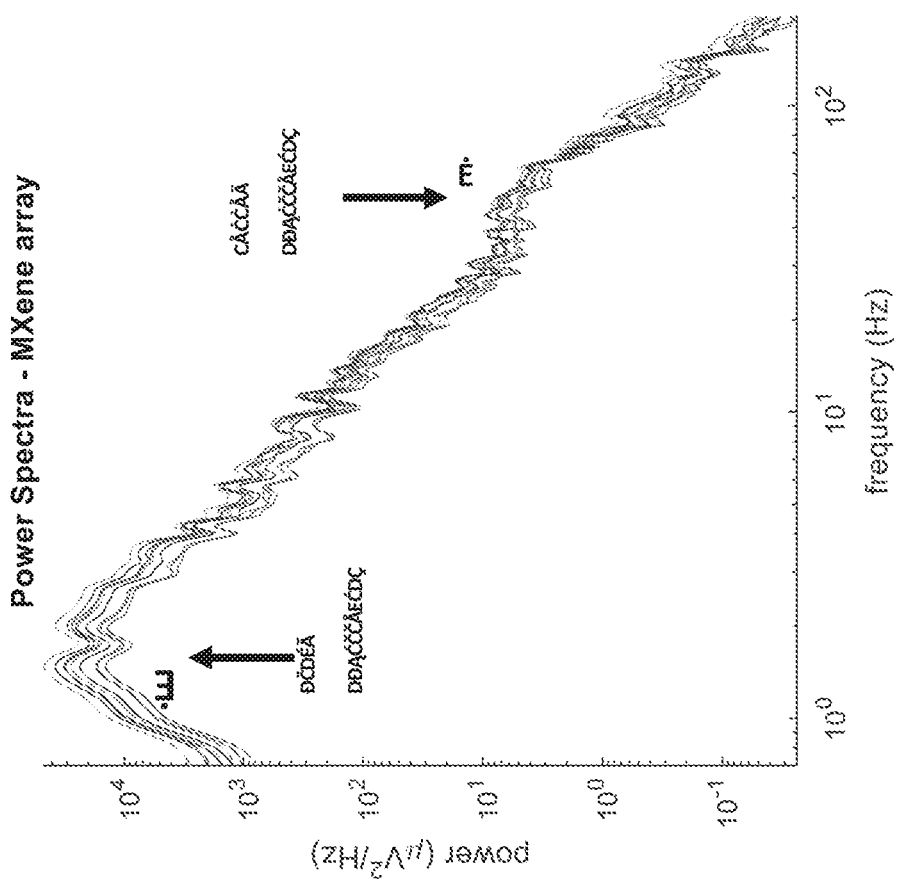
Figure 8C:
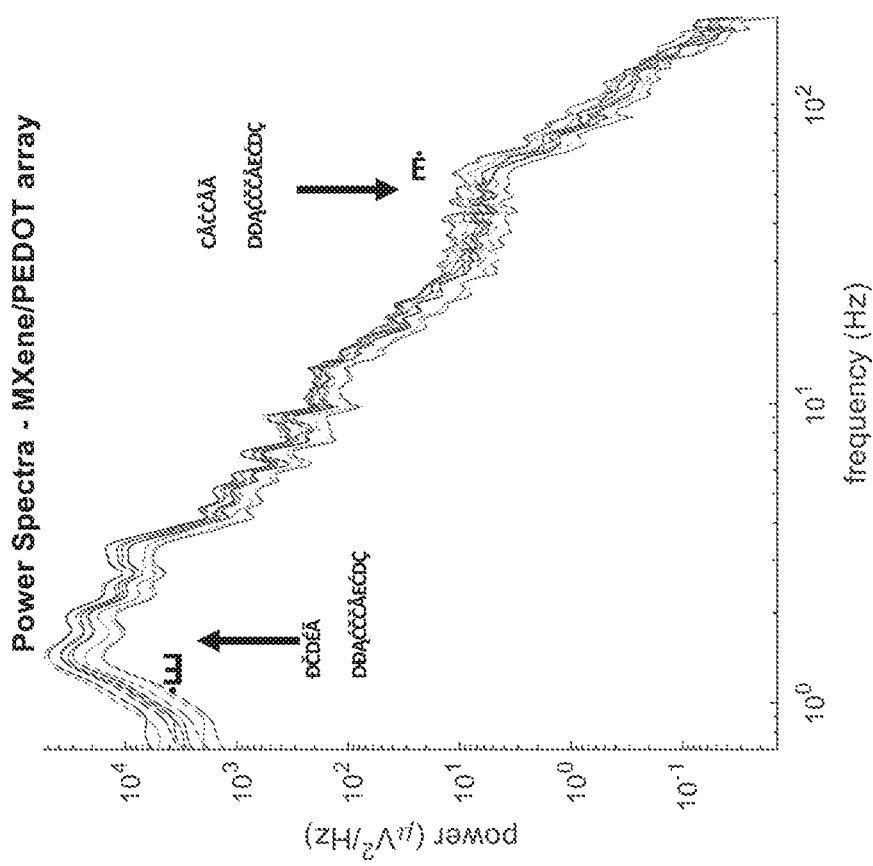
Figure 10A:
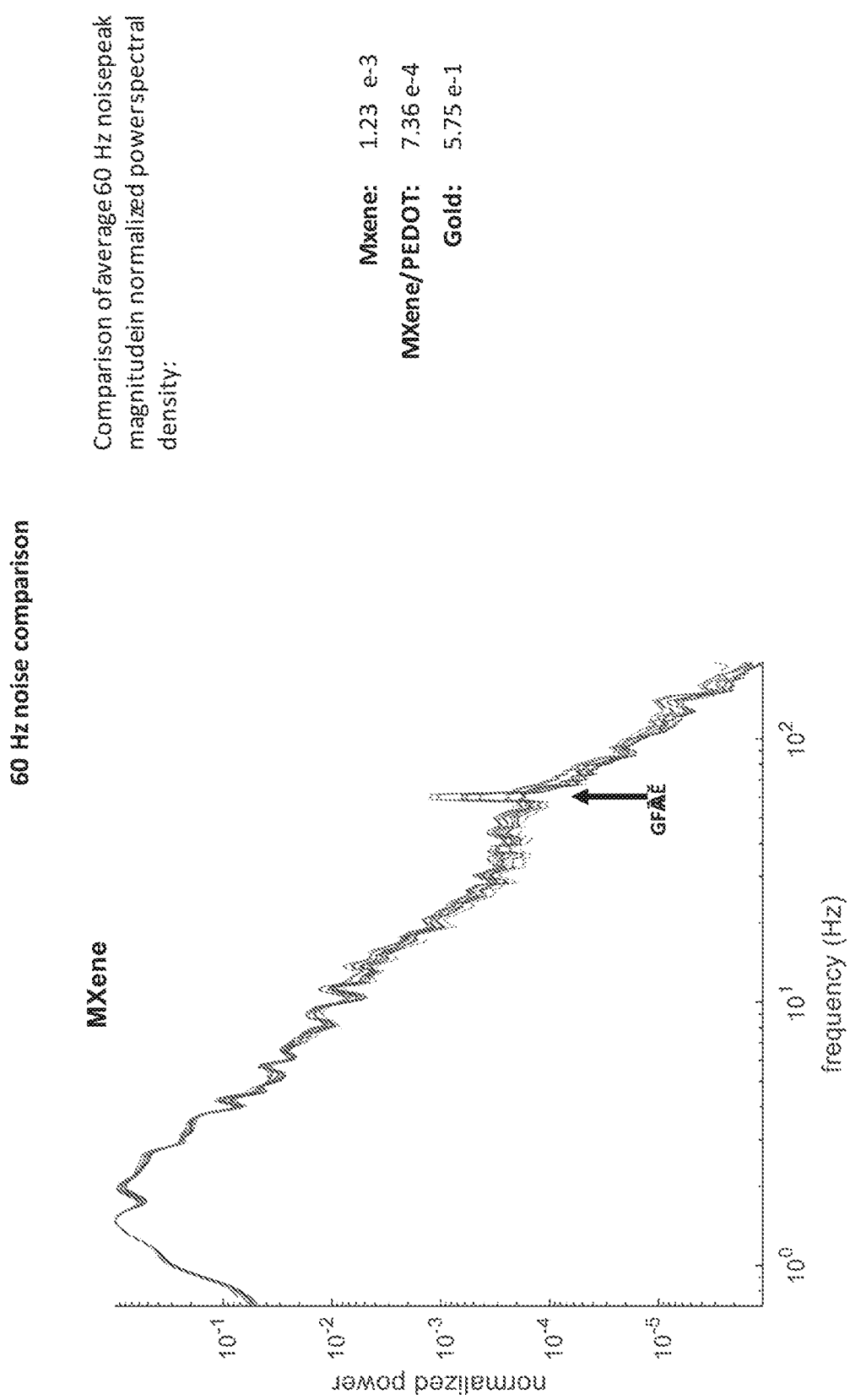
FIGS. 10A, 10B, and 10C show 60 Hz noise for MXene and other devices.
Figure 10B:
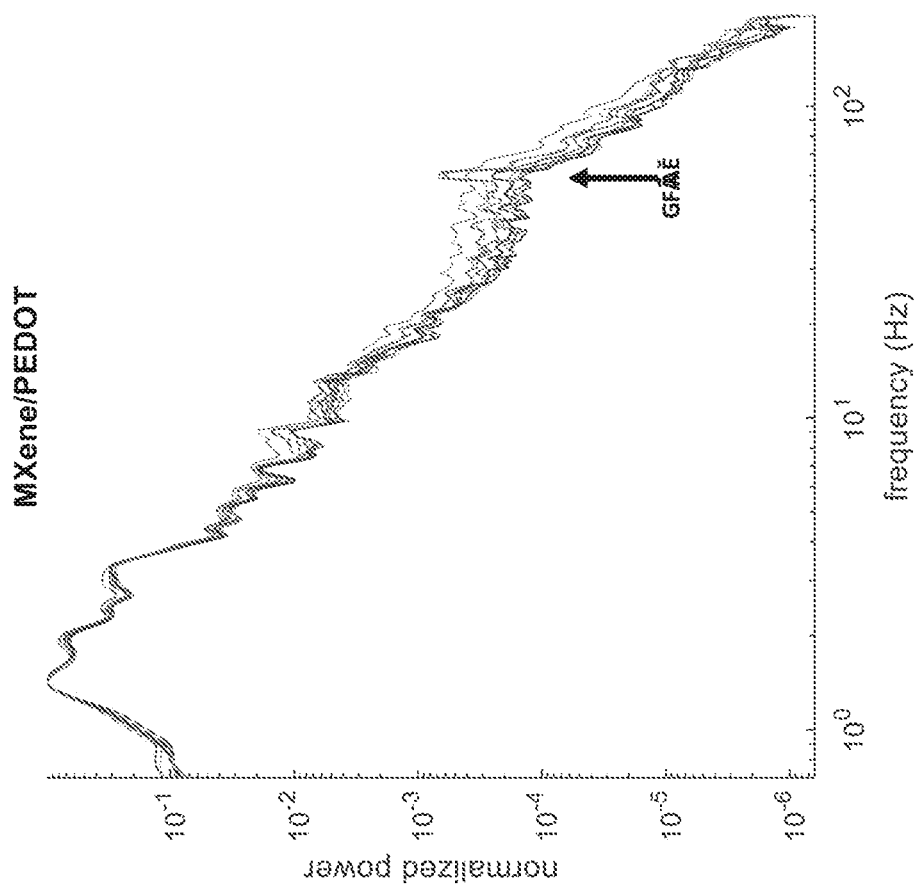
Figure 10C:
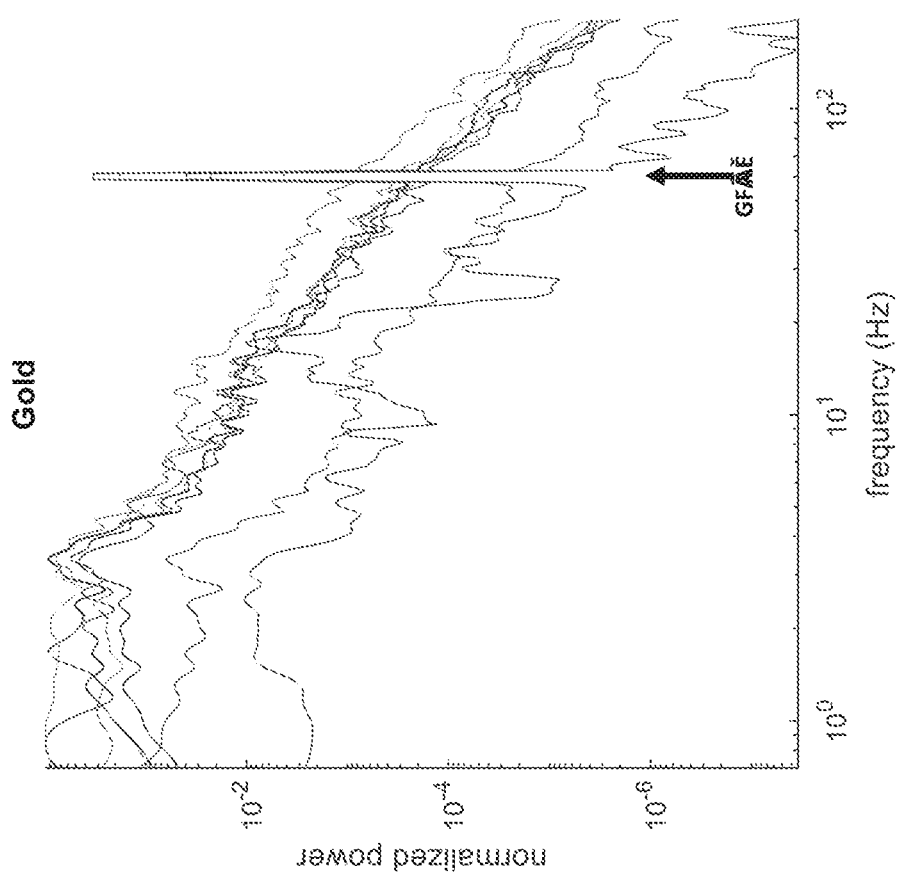
Figure 11B:
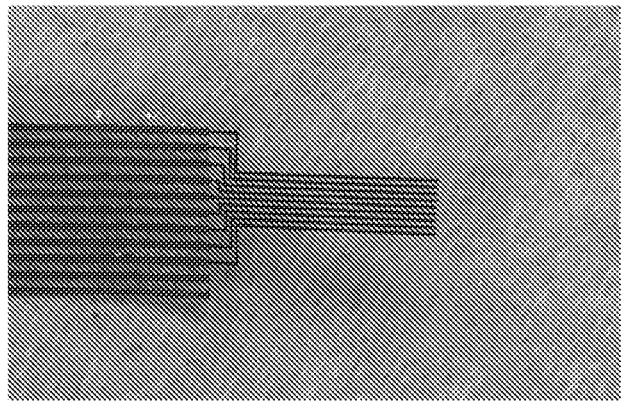
FIGS. 11A and 11B show example transparent MXene neural sensors.
Figure 11A:
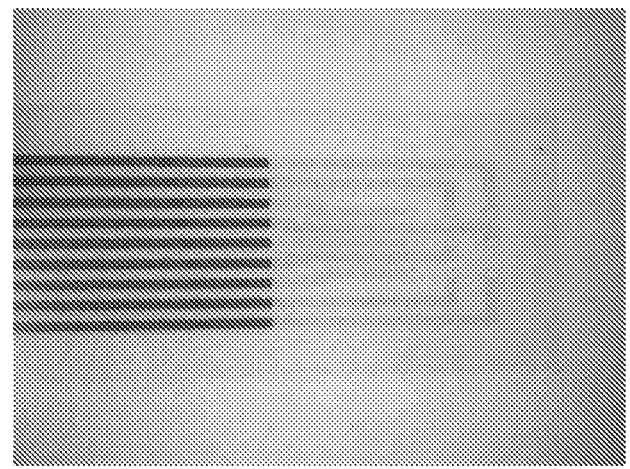
Figure 12B:
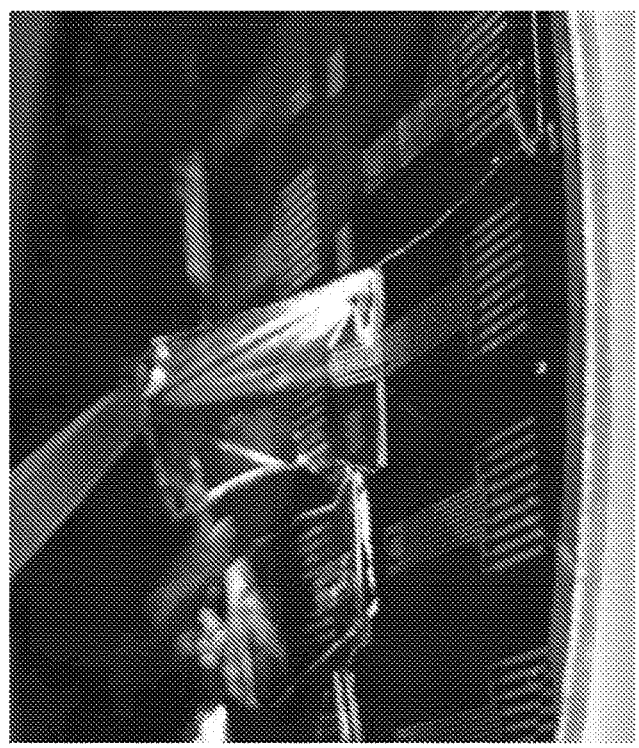
FIGS. 12A, 12B, and 12C are photographs of example MXene electrodes.
Figure 12A:
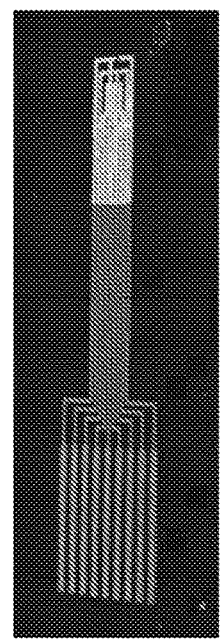
Figures 1, 12C:
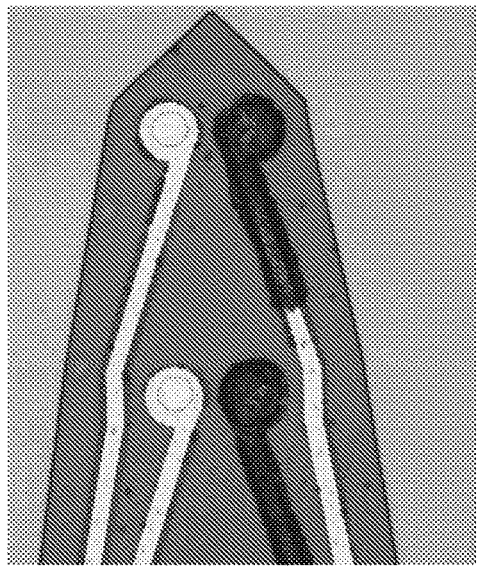
Figures 2, 12C:
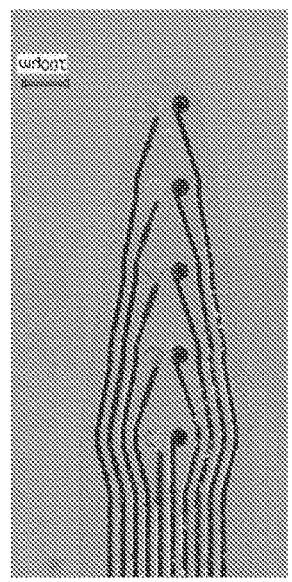
Figures 2, 12C:
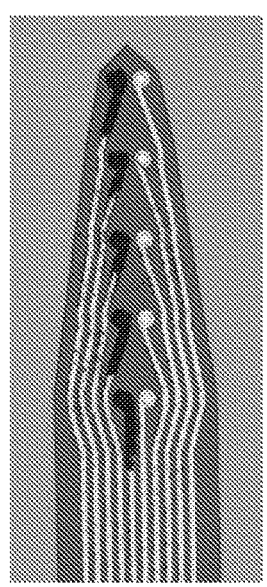
Figure 13A:
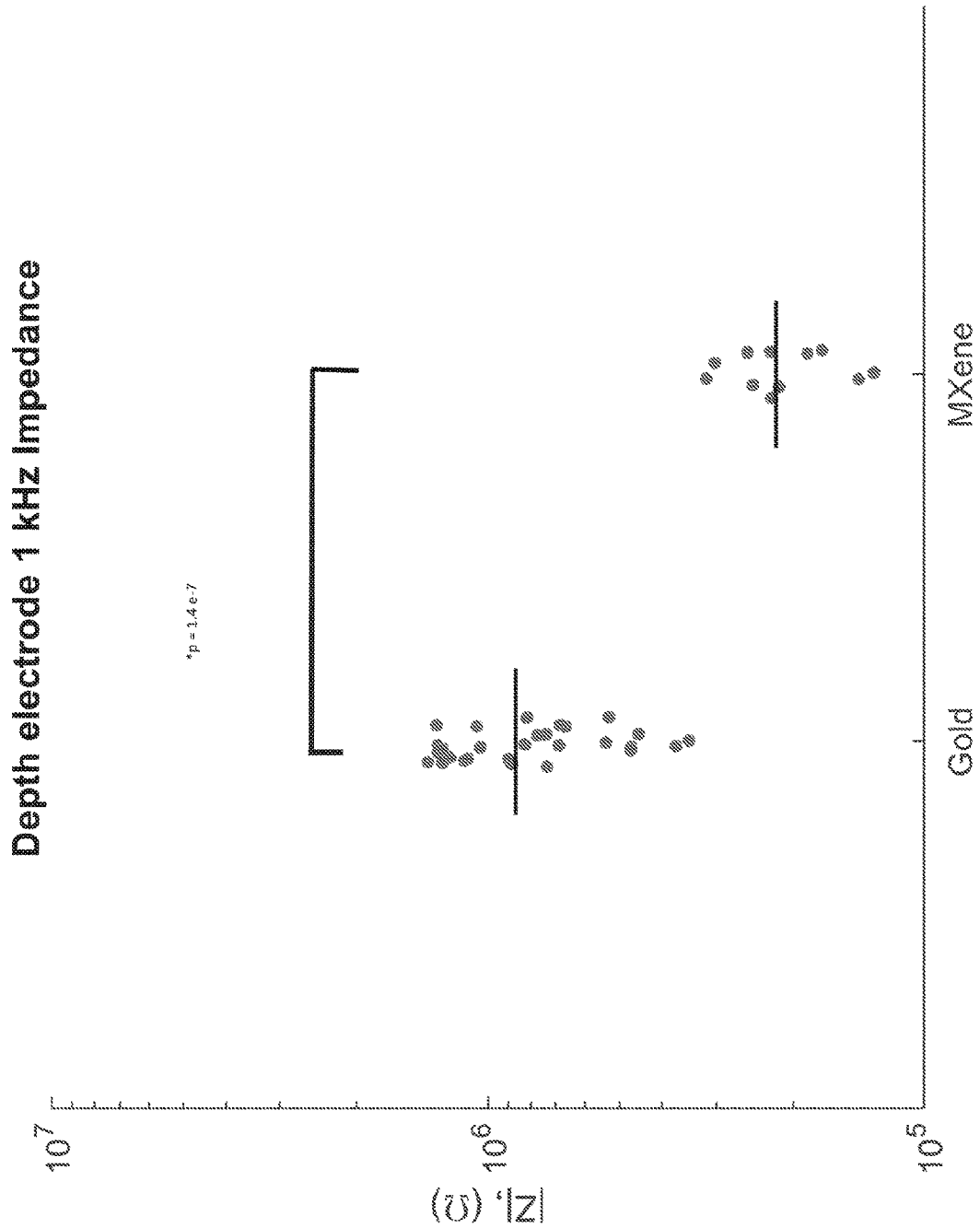
Figure 14:
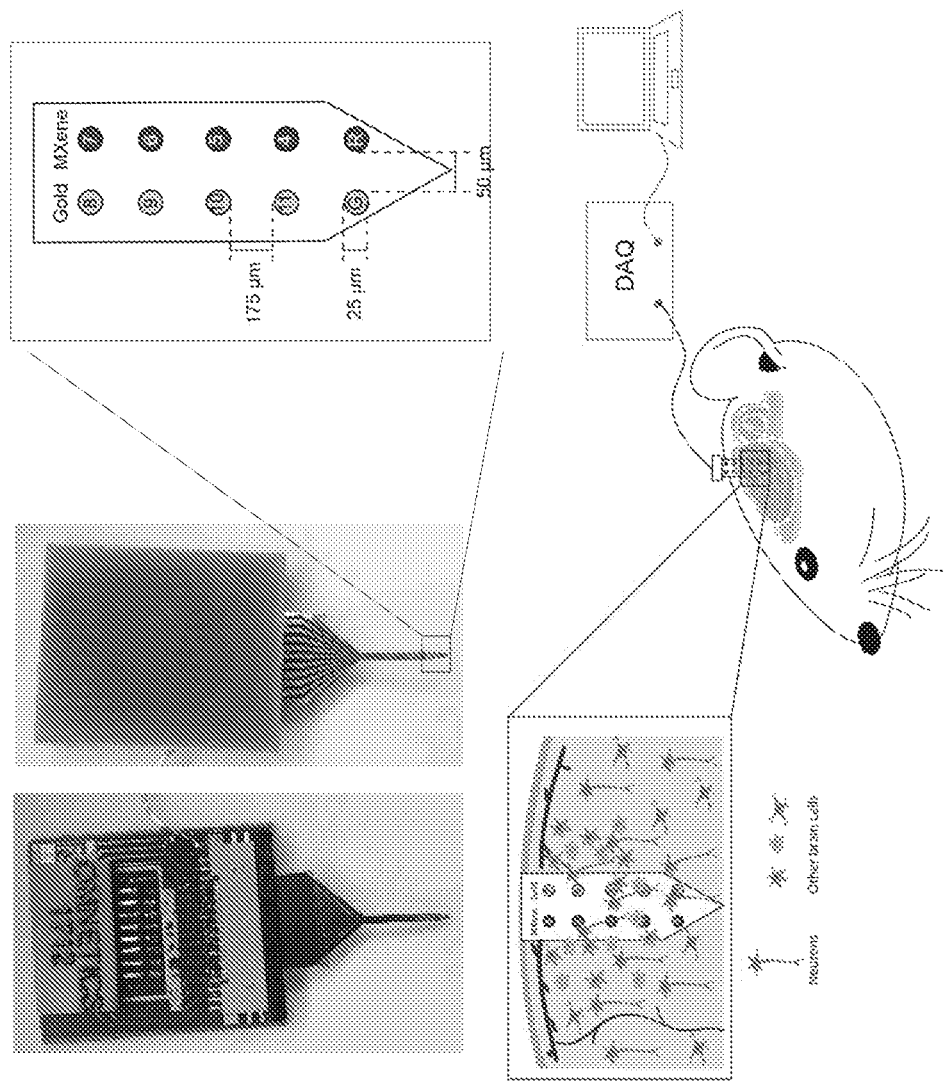
FIG. 14 describes in vivo recordings using example electrodes.
Figure 15B:
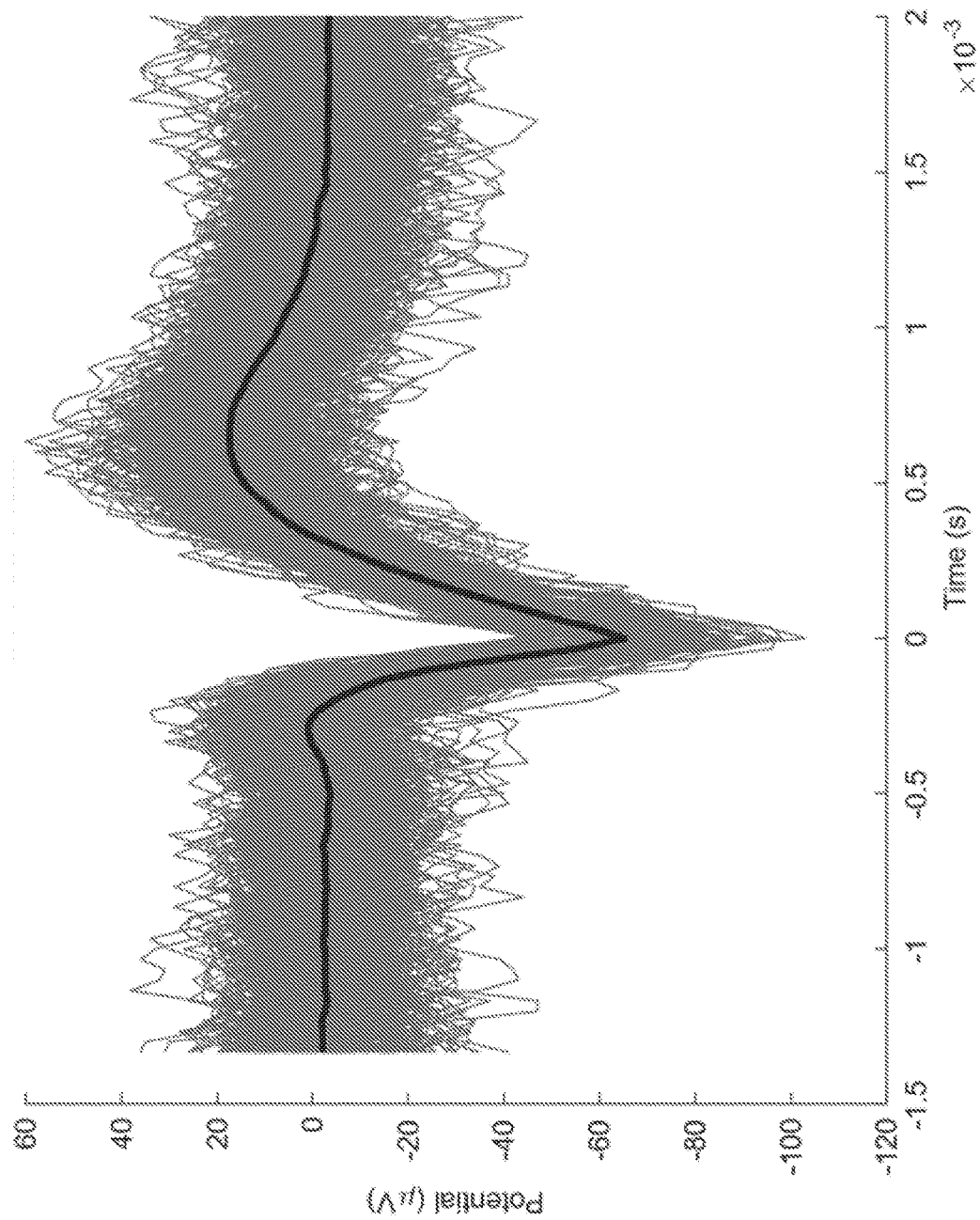

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise. As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps. It is to be understood that the terminology used herein is for the purpose of describing particular aspects only and is not intended to be limiting. As used in the specification and in the claims, the term "comprising" can include the embodiments "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams (g) to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

Electrodes and other devices including MXenes-based conductive elements may be created for implantation in, or placement outside on the body of, a living subject. MXenes are a family of two-dimensional metal carbides and nitrides such as $Ti_2C$, $Mo_2C$, $Ti_3C_2$, and the like. See United States published patent application US2014/0162130 (Barsoum, et al.), titled "Compositions Comprising Free-Standing Two-Dimensional Nanocrystals," published Jun. 12, 2014 the content of which is hereby incorporated herein by reference in its entirety. Suitable MXene materials are also described in, e.g.: WO2012177712A1 (Barsoum, et al.) titled "Compositions comprising free standing two dimensional nanocrystals" published Dec. 12, 2012; WO2016049109A2 (Ghidu, et al.) titled "Physical forms of MXene materials exhibiting novel electrical and optical characteristics" published Mar. 31, 2016; WO2014088995A1 (Barsoum, et al.) titled "Compositions comprising free-standing two-dimensional nanocrystal" published Jun. 12, 2014; WO2017011044A2 (Barsoum, et al.) titled "Two-dimensional, ordered, double transition metals carbides [ . . . ]" published Jan. 19, 2017; and WO2016140948A1 (Barsoum, et al.) titled "Nanolaminated 2-2-1 max-phase compositions" published Sep. 9, 2016, the content of which are hereby incorporated by reference.

MXenes may be from carbides of transition metals, and take the form of nanomaterials, such as 2D nanomaterials. For example, MXenes may be assembled from aqueous solution into optically transparent thin films with conductivity surpassing other 2D materials, such as graphene.

The term "electrode" here refers to a transducer that connects the body to a device used for receiving or transmitting electrical signals. These electrodes can be used in several applications, including neural electrodes for the central, peripheral nervous and neuromuscular systems, and electrodes for cardiac rhythm management systems, in addition to other applications for electrical and/or chemical or biological sensing and stimulation.

MXenes are a new class of materials that offer a unique combination of electrical conductivity, strength, flexibility, and volumetric capacitance (e.g., 1500 $F/cm^3$). See Lukatskaya, M. R. et al. Ultra-high-rate pseudocapacitive energy storage in two-dimensional transition metal carbides. *Nature Energy* 6, 17105 (2017), the contents whereof is hereby incorporated by reference. Furthermore, by varying processing parameters, the optical transparency of MXenes can be tuned to >90% at wavelengths >400 nm. Thanks to the combination of microscale-roughness and high-capacity, the electrochemical impedance of MXene neural sensors measured at 1 kHz is at least 4 times smaller than that of gold electrodes of the same size. When used for recording of neural signal in vivo, this reduction in electrochemical impedance results in significant suppression of line noise from electrical interference (>400-fold reduction compared to gold electrodes) and from electronic noise in the electrode itself (50% less than gold).

The use of MXenes as biomaterials for high-resolution, low-noise, minimally invasive electrodes and devices can find applications in a wide variety of devices, including pacemaker electrodes, deep brain stimulation (DBS) electrodes, BMI (brain-machine interface) electrodes, intracranial EEG electrodes, and penetrating intra-cortical electrode arrays, such as Utah-type arrays or Michigan-type arrays. They may also be used throughout the body for bio-electronic devices to interface with peripheral nerves, muscle and other organs and electrochemically active tissues. The electrodes may be used for electrophysiological research and clinical functional treatments, including brain stimulation (e.g., Parkinson's disease, essential tremor, obsessive compulsive disorder, dystonia, and epilepsy), and stimulation of muscles and peripheral nerves (e.g., chronic pain, gastroparesis, bowel incontinence, overactive bladder, urinary retention, and severe spasticity).

The following provides illustrative disclosure only and does not limit the scope of the present disclosure or of the attached claims.

Example 1

A prototype multi-electrode sensor for recording neural signals was created and tested. The sensor consists of 9 electrode contacts, each 50 μm×50 μm in size. The sensor was fabricated using microfabrication techniques, including physical vapor deposition of insulating polymer layers and metal traces, photolithography and lift-off to pattern the metal traces, a dry lift-off technique to form the MXene patterns, and oxygen plasma reactive ion etching to form the outline of the device and the electrode openings in the top polymer layer.

Electrochemical impedance spectroscopy was performed using a potentiostat, which measurement revealed a 1 kHz impedance of 48±35 kΩ for the MXene electrodes, a value significantly reduced from gold electrodes of the same dimensions, which had a mean 1 kHz impedance magnitude of 200±100 kΩ. The MXene electrodes were tested in vivo in an anesthetized rat, where they were placed on the exposed cortex. The sensor successfully recorded physiological signals from the rat's brain in all 9 electrode channels. Analysis of the in vivo data showed significantly reduced baseline noise when compared to gold electrodes of the same size, with a baseline noise level of 3.7 μVrms for the MXene electrodes compared to 6.6 μVrms for comparable gold electrodes.

Transparency

The transparency of MXene films has been verified via spectroscopy in the UV/visible wavelength range. Thin (5-30 nm) MXene films have transparency >50% at in the 350<lambda<550 nm range, which spans the range of wavelengths compatible with excitation/emission of fluorescent probes commonly used in neurophysiology research (i.e., calcium imaging and optogenetics, lambda<490 nm) and visible light (lambda=550 nm). Specifically, 5 nm thick films have transparency >90% in the in the 350<lambda<550 nm range, which means that they are virtually completely transparent.

The conductivity of MXene films is ~2× than that of graphene films with the same transparency, which is a major advantage for neurophysiology applications where the conductivity of the electrodes can significantly impact the noise levels in the recordings.

Flexibility

The flexibility of MXene electrodes can be quantified with the bending modulus, which is calculated as: k=EI, where E is the Young's modulus, I is the area moment of inertia. For probes with rectangular cross section, I=wt$^3$, where w is the width and t is the thickness. Thus, the bending stiffness is a function of both the tensile and geometric properties of the probes.

For example, for an electrode with a MXene film is that is ~200-300 nm, which may be approximately 2% of the total thickness of a parylene substrate and encapsulation layer. Thus, it is reasonable to assume that the total bending stiffness is controlled by the geometry and tensile properties of the parylene structure. For one exemplary prototype, depth of electrodes w=405 micron, t=10 micron, k=9*10^-11 N*m^2, which is 150 to 1000 smaller than the bending stiffness of silicon and metal microelectrodes currently used in animal research and brain-computer interface implants in humans.

Variations

MXenes may be use directly as electrode material, without any metal layer underneath. For example, a MXene film may make contact with gold traces used as conductors for connection to a printed circuit board, and thereby to a data acquisition system. The gold does not need to be exposed on the electrode contact surface, but rather may be found only under the parylene encapsulation layer such that the gold does not contribute to the electrode performance at MXene-tissue interface.

Electrode dimensions may vary widely depending on intended use. The selected size may depend, for instance, on the specific application, recording location, and bandwidth of the recorded signal. For high-resolution, high signal-to-noise ratio (SNR) neural recordings at the spatiotemporal scale of individual neuronal action potential (1-10 ms, 10-100 micron) the size of the electrode may be comparable with that of the neuronal body (~15-30 micron), for example, where the impedance the electrode interface may be in the range of ~200-600 k Ohm at the reference frequency of 1 kHz.

Micro-fabrication and nano-fabrication techniques, such as e-beam lithography, allow the creation of submicron scale features, e.g., in the body of the electrode, or for gripping/tendril projections from an electrode body to enhance surface area or mechanical bonding to a living structure, for example.

Electrodes may be made of composite materials comprising MXenes and conductive polymers. For example, composite may be formed using polythiophenes such as poly(3,4-ethylenedioxythiophene) (PEDOT) and poly(3,4-ethylenedioxythiophene) polystyrene sulfonate (PEDOT-PSS), polyaniline (PANT), polypyrrole (PPY), and similar materials.

Additional disclosure is found in the attached appendices, which appendices are part of this disclosure and are incorporated herein in their entireties for any and all purposes.

EXEMPLARY EMBODIMENTS

Embodiment 1

An electrode, comprising an exposed contact surface, the exposed surface comprising a contact material, the contact material comprising a MXene.

Embodiment 2

The electrode of embodiment 1, wherein the wherein the MXene is selected from the MXene family, for example $Ti_2C$, $Mo_2C$, and $Ti_3C_2$.

Embodiment 3

The electrode of embodiment 1, wherein a width of the exposed contact surface is less than about 100 um across.

Embodiment 4

The electrode of embodiment 1, wherein a width of the exposed contact surface is less than about 50 um across.

Embodiment 5

The electrode of embodiment 1, wherein a width of the exposed contact surface is less than about 10 um across.

Embodiment 6

The electrode of embodiment 1, wherein a width of the exposed contact surface is less than about 1 um across.

Embodiment 7

The electrode of any of embodiments 1-6, wherein the exposed contact surface is shaped to penetrate a single neural fiber.

Embodiment 8

The electrode of any of embodiments 1-7, wherein the electrode is at least about 40% transparent to light with a wavelength of about 400 nm, as measured perpendicular to the exposed contact surface.

Embodiment 9

The electrode of embodiment 8, wherein the electrode is at least about 90% transparent to light with a wavelength of about 400 nm, as measured perpendicular to the exposed contact surface.

Embodiment 10

The electrode of any of embodiments 1-9, wherein the contact material further comprises a conductive polymer.

Embodiment 11

The electrode of embodiment 10, wherein the conductive polymer comprises a polythiophene.

Embodiment 12

The electrode of embodiment 10, wherein the conductive polymer is selected from the list consisting of: poly(3,4-ethylenedioxythiophene); poly(3,4-ethylenedioxythiophene); polystyrene sulfonate; polyaniline; and polypyrrole.

Embodiment 13

The electrode of any of embodiments 1-12, wherein the electrode is incorporated into a device configured to monitor signals related to neural activity, muscular activity, cardiac activity, or combinations thereof.

Embodiment 14

The electrode of any of embodiments 1-13, wherein the electrode is characterized as having a mean 1 kHz |Z| of less than about 60 kilo-ohms.

Embodiment 15

The electrode of any of embodiments 1-14, wherein the electrode is characterized as having an impedance, at 1 kHz, that is less than about 50% the impedance of a comparable gold electrode that is free or essentially free of the MXene.

Embodiment 16

The electrode of embodiment 15, wherein the electrode is characterized as having an impedance, at 1 kHz, that is less than about 25% the impedance of a comparable gold electrode that is free or essentially free of the MXene.

Embodiment 17

The electrode of any of embodiments 1-16, wherein the electrode is characterized as having a standard deviation of background noise of less than about 5 μVrms when operating in the neural spike band of frequencies.

Embodiment 18

The electrode of any of embodiments 1-17, wherein the electrode is characterized as having an average 60 Hz noise peak magnitude in a normalized power spectral density of less than about $1 \times 10^{-1}$.

Embodiment 19

A method, comprising: using an electrode according to any of embodiments 1-18 in connection with monitoring one or more signals related to neural activity, muscular activity, cardiac activity, or combinations thereof.

Embodiment 20

A method, comprising incorporated an electrode according to any of embodiments 1-19 into a device that is configured to perform monitoring one or more signals related to neural activity, muscular activity, cardiac activity, or combinations thereof.

What is claimed:

1. An electrode, comprising:
   an exposed contact surface, the exposed contact surface comprising a contact material, the contact material comprising a MXene, and
   the electrode being configured to monitor a signal related to neural activity, muscular activity, cardiac activity, or combinations thereof.

2. The electrode of claim 1, wherein a width of the exposed contact surface is less than 100 um across.

3. The electrode of claim 1, wherein a width of the exposed contact surface is less than 10 um across.

4. The electrode of claim 1, wherein the exposed contact surface is shaped to penetrate a single neural fiber.

5. The electrode of claim 1, wherein the electrode is at least 40% transparent to light with a wavelength of 400 nm, as measured perpendicular to the exposed contact surface.

6. The electrode of claim 5, wherein the electrode is at least 90% transparent to light with a wavelength of 400 nm, as measured perpendicular to the exposed contact surface.

7. The electrode of claim 1, wherein the contact material further comprises a conductive polymer.

8. The electrode of claim 7, wherein the conductive polymer is a polythiophene.

9. The electrode of claim 1, wherein the electrode is incorporated into a device configured to monitor signals related to neural activity, muscular activity, cardiac activity, or combinations thereof.

10. The electrode of claim 1, wherein the electrode is characterized as having an impedance at 1 kHz of less than about 60 kilo-ohms.

11. The electrode of claim 1, wherein the electrode is characterized as having an impedance, at 1 kHz, that is at least 40% less than impedance of a comparable electrode, where the comparable electrode has a contact surface of the same size and shape of the exposed contact surface of the electrode, and where the contact surface of the comparable electrode consists of gold.

12. The electrode of claim 1, wherein the electrode is characterized as having a standard deviation of background noise of less than about 5 μVrms when operating in neural spike band of frequencies.

13. The electrode of claim 1, wherein the electrode is characterized as having an average 60 Hz noise peak magnitude in a normalized power spectral density of less than about $1\times10^{-1}$.

14. A device, comprising: a plurality of electrodes, each of the plurality of electrodes comprising an exposed contact surface, the exposed contact surface comprising a contact material, the contact material comprising a MXene.

15. A method, comprising: implanting into a subject a device that comprises an electrode that comprises an exposed contact surface, the exposed contact surface comprising a contact material that comprises a MXene.

16. The method of claim 15, wherein the device comprises a plurality of electrodes each electrode comprising an exposed contact surface, the exposed contact surface comprising a contact material, the contact material comprising a MXene.

17. A method, comprising: collecting a physiological signal from a subject with at least one electrode that comprises an exposed contact surface, the exposed contact surface comprising a contact material that comprises a MXene.

18. The method of claim 17, further comprising collecting physiological signals from a plurality of locations within the subject with a plurality of electrodes, each electrode comprising an exposed contact surface, the exposed contact surface comprising a contact material that comprises a MXene.

19. A method, comprising: delivering electrical stimulation to a subject with an electrode that comprises an exposed contact surface, the exposed contact surface comprising a contact material that comprises a MXene.

20. The method of claim 19, wherein the delivering is performed with a plurality of electrodes, each electrode comprising an exposed contact surface, the exposed contact surface comprising a contact material, the contact material comprising a MXene.

* * * * *

UNITED STATES PATENT AND TRADEMARK OFFICE
CERTIFICATE OF CORRECTION

PATENT NO. : 11,925,466 B2
APPLICATION NO. : 16/646662
DATED : March 12, 2024
INVENTOR(S) : Flavia Vitale et al.

It is certified that error appears in the above-identified patent and that said Letters Patent is hereby corrected as shown below:

On the Title Page

Item (72) In Inventors,

Under Column No. 1, Line no. 5, Replace:
"Fisher"
With:
--Fishers--

Item (56) In Other Publications,

Under Column No. 2, Page 2, Line no. 13, Replace:
"Neural Acivity", Adv."
With:
--Neural Activity", Adv.--

Under Column No. 2, Page 2, Line no. 16, Replace:
"Vitale eta l.,"
With:
--Vitale et al.,--

In the Specification

Under Column No. 1, Line no. 40, Replace:
"from which from individual"
With:
--from which individual--

Under Column No. 1, Line no. 65, Replace:
"combinations thereof"

Signed and Sealed this
Second Day of July, 2024

Katherine Kelly Vidal
*Director of the United States Patent and Trademark Office*

CERTIFICATE OF CORRECTION (continued)
U.S. Pat. No. 11,925,466 B2

With:
--combinations thereof.--

Under Column No. 2, Line no. 32, Replace:
"ketamine-dexmetomidine anesthesia."
With:
--ketamine-dexmedetomidine anesthesia.--

Under Column No. 6, Line no. 56, Replace:
"100 um across."
With:
--100 μm across.--

Under Column No. 6, Line no. 61, Replace:
"50 um across."
With:
--50 μm across.--

Under Column No. 6, Line no. 67, Replace:
"10 um across."
With:
--10 μm across.--

Under Column No. 7, Line no. 4, Replace:
"1 um across."
With:
--1 μm across.--

Under Column No. 7, Line nos. 39-40, Replace:
"poly(3,4-ethylenedioxythiophene); polystyrene"
With:
--poly(3,4-ethylenedioxythiophene) polystyrene--

In the Claims

Under Column No. 8, Claim 2, Line no. 39, Replace:
"100 um across."
With:
--100 μm across.--

Under Column No. 8, Claim 4, Line no. 41, Replace:
"10 um across."
With:
--10 μm across.--

CERTIFICATE OF CORRECTION (continued)
U.S. Pat. No. 11,925,466 B2

Under Column No. 9, Claim 16, Line no. 18, Replace:
"electrodes"
With:
--electrodes,--